United States Patent [19]

Pasedach et al.

[11] 4,064,393

[45] Dec. 20, 1977

[54] DEVICE FOR MEASURING RADIATION ABSORPTION IN A SECTION OF A BODY

[75] Inventors: Klaus Pasedach, Hamburg; Wolfgang Wagner, Norderstedt, both of Germany

[73] Assignee: U.S. Philips Corporation, New York, N.Y.

[21] Appl. No.: 661,986

[22] Filed: Feb. 27, 1976

[30] Foreign Application Priority Data

Mar. 14, 1975 Germany .................................. 2511231

[51] Int. Cl.$^2$ ............................................ G01N 23/08
[52] U.S. Cl. ........................... 364/414; 250/445 T
[58] Field of Search ................ 235/151.3; 250/445 T; 444/1

[56] References Cited

U.S. PATENT DOCUMENTS 3,878,373  4/1975  Blum ................................. 235/151.3
3,987,281  10/1976  Hodes ............................... 235/151.3

Primary Examiner—Edward J. Wise
Attorney, Agent, or Firm—Frank R. Trifari; Carl P. Steinhauser

[57] ABSTRACT

A device for examining a body section by means of x-radiation including a plurality of detectors arranged to intercept radiation passing through the body in straight lines or strips and a calculating circuit which interpolates, on the basis of absorption values measured, absorption values which can be expected along sets of mutually extending strips which cross each other at different angles. The absorption in the section of the body can then be calculated in known manner on the basis of these values.

11 Claims, 4 Drawing Figures

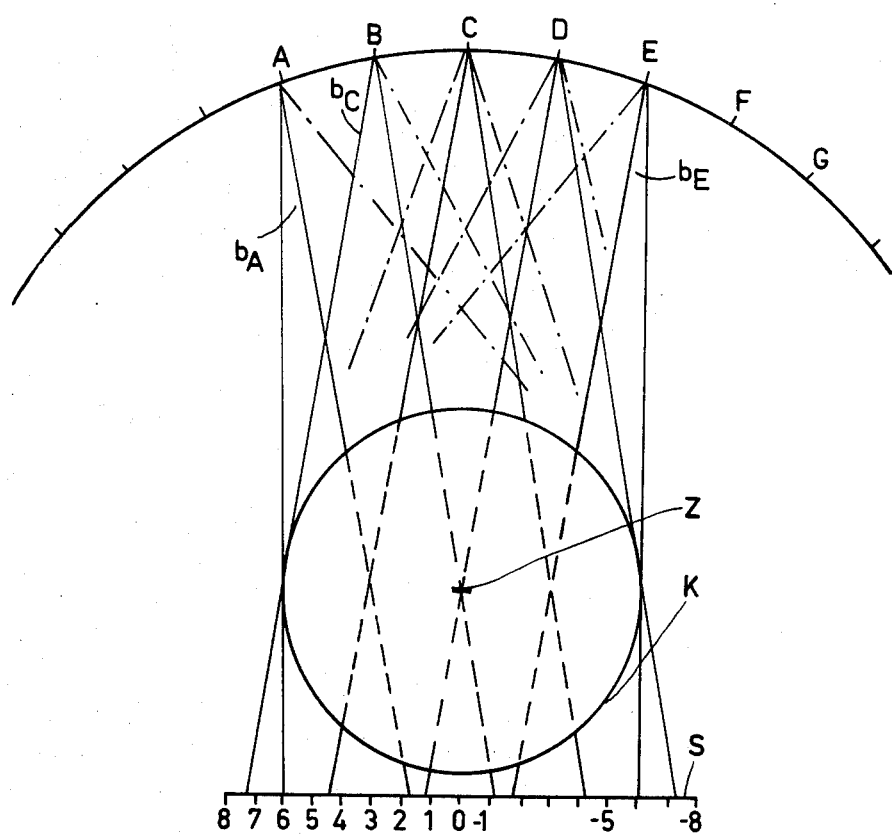
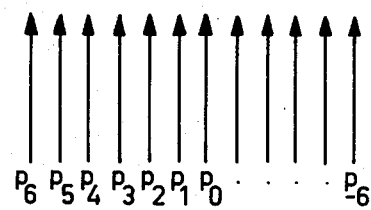
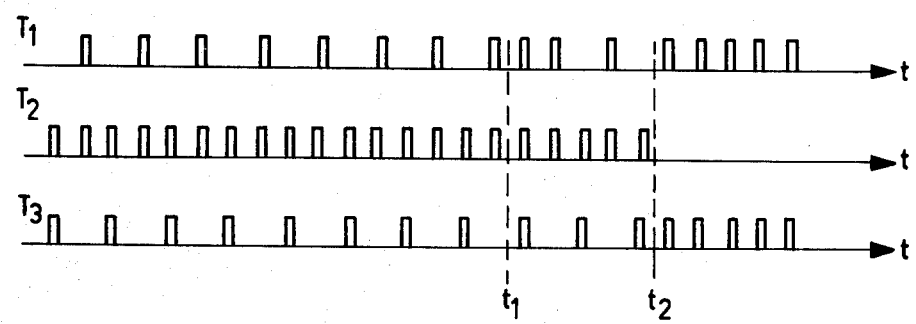
Fig. 1
Fig. 4

DEVICE FOR MEASURING RADIATION ABSORPTION IN A SECTION OF A BODY

The invention relates to a device for measuring radiation absorption in a section of a body, comprising a radiation source emitting a wedge-shaped flat beam which irradiates the body, a series of adjacently arranged radiation detectors for the local measurement of a transmitted part of the radiation in different positions of the source and the detectors with respect to the body, and a calculating device for calculating the absorption in the section to be measured on the basis on the measuring values obtained.

A device of this kind is known, for example, from German Offenlegungsschrift No. 2,426,343. It has been found that in a device described therein the calculation of the absorption in the section is more inaccurate as the angle between the two outer rays of the stopped radiation beam is larger. This error could be minimized by choosing the distance between the body and the radiators to be as large as possible, but in that case the radiation intensity would have to be substantially increased; this is undesirable from a medical point of view and, moreover, usually cannot this be realized or can be realized only with great difficulty if an X-ray tube is used as the radiation source.

An object of the invention is to provide a device enabling correct calculation also in the case of a small distance between radiator and object, i.e. in the case of a wide angle between the two outer rays of the stopped radiation beam. To this end, a device of the kind set forth according to the invention is characterized in that there is provided a calculating circuit which calculates integral values of the absorption along mutually crossing sets of mutually parallel extending strips by interpolation of measuring values, the integral values being processed by the calculating device for measuring the absorption in the section of the body.

It is to be noted that it is known per se (from German Offenlegungsschrift No. 1,941,433) to utilize the integral values of the absorption along mutually crossing sets of parallel extending strips for calculating the absorption of radiation in a section of a body. These integral values are measured by using a radiator and a single radiation detector. The attenuation of the radiation emitted by the radiator, measured behind the body by means of the single radiation detector, is proportional to the expontential function of the integral of the absorption along the straight line described by the ray. The integral values of the other strips extending parallel thereto are measured by a displacement of the radiator/radiation detector system in the direction perpendicular to the beam path. This method enables very accurate calculation of the absorption in the section, because each time use is made of the measuring values or integral values measured along parallel straight lines or strips, but a major drawback with respect to the described device exists in that in a given position of the X-radiator always only one measuring value can be measured, while in the device of the kind set forth as many measuring values can be measured in a position of the radiator as there are radiation detectors, for example, 100. Consequently, in a device as described in the German Offenlegungsschrift No. 1,941,433 the measurement of all necessary measuring values requires substantially more time than in a device of the kind set forth.

In a device in which the radiation detectors are rotated through an angle of 180° or less for measuring the measuring values, the calculation of the integral values from the measuring values is effected in accordance with the invention in that the calculation device forms the integral values by interpolation of measuring values recorded in two adjoining positions between which the strip each time extends.

However, if use is made of a device in which the radiator/radiation detector system is rotated through an angle of more than 180°, preferably 360°, for measuring the measuring values, the calculation of the integral values from the measuring values can be effected in accordance with the invention in that the calculating device forms the integral values by interpolation of measuring values recorded in four positions, each time two positions thereof being adjacent and enclosing the strip to be calculated.

Both embodiments have in common that each time the measuring values are obtained from the neighbouring positions of the radiator/radiation detector system (if the angle of rotation is less than 360°, the two outer positions are considered to be adjacent) between which the strip along which the integral value is to be calculated extends or which enclose the smallest angle with this strip.

One embodiment of the device in accordance with the invention will be described in detail hereinafter, by way of example, with reference to the drawing.

FIG. 1 shows the geometrical relationships in a device in accordance with the invention.

FIG. 4 shows the time sequence of the clock pulses for controlling the calculating circuit shown in FIG. 3.

Figure 2:
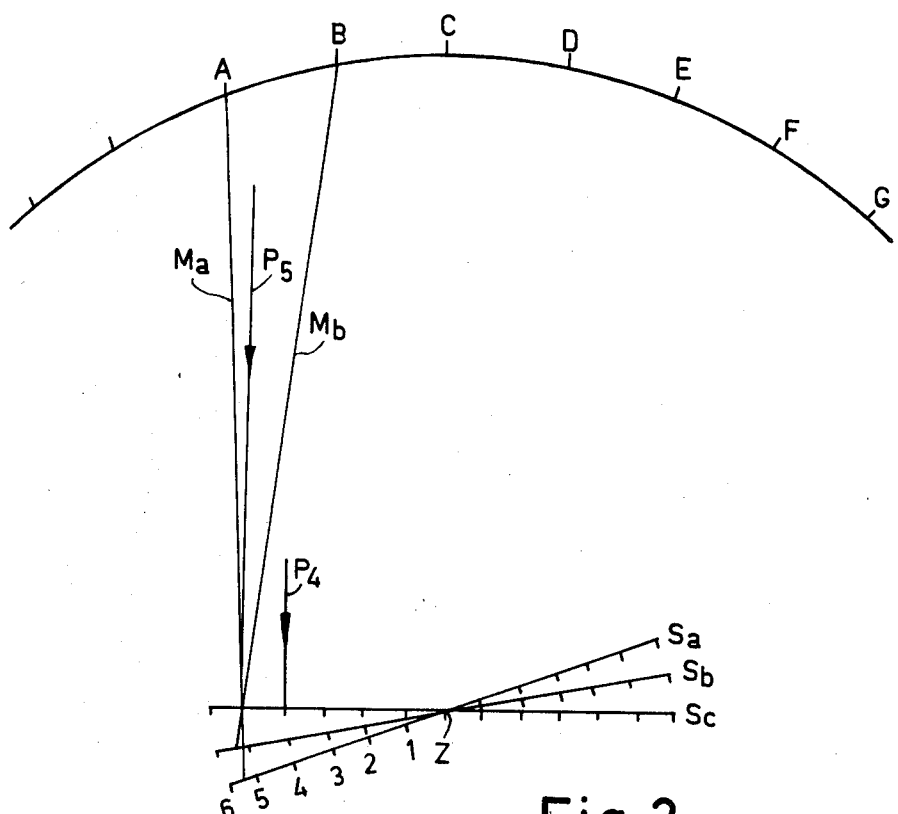
FIG. 2 shows a modified detail of FIG. 1 to illustrate the calculation of the integral values from the measuring values.

The reference K in FIG. 1 denotes a section of the body for which the absorption values are to be measured. A radiator, for which the drawing shows only wedge-shaped stopped beams $b$, can be rotated, together with a series S of adjacently arranged radiation detectors which are denoted in the drawing by the references 8 ... −8 and which are rigidly connected to the radiator, about the rotary axis Z which is perpendicular to the plane of the drawing, it being possible for the system to occupy different positions, some of which are denoted by the references A to G in the drawing. In practice a larger number of radiation detectors will be used, for example, 100 detectors. The series of radiation detectors S is shown in the position occupied when the radiator is in the position C. In the other positions of the radiator, the series S will be rotated accordingly about the point Z.

The measuring values measured by the radiation detectors are an exponential function of the integral of the absorption along the straight connection line between the radiator and the detector (on the basis of the finite dimensions of the radiator and the detectors, this "straight line" is actually a strip). Because the calculation of the absorption in the section cannot be effected on the basis of the exponential value of the integral but only on the basis of the integral itself, the integral values must be converted into logarithms; consequently, the term "measuring value" used herein is to be understood to mean the value produced by the logarithmic conversion of the output signal of a radiation detector.

As has already been stated, the measuring values obtained on the basis of diverging radiation beams are not directly used for calculating the absorption; the calculation is actually performed on the basis of the absorption along mutually crossing sets of parallel extending strips.

FIG. 1 shows such a set of parallel extending strips ($P_6 \ldots P_{-6}$) which are shown as a straight line for the sake of simplicity. The integral values along these straight lines or strips are formed by interpolation of measuring values recorded in two adjoining positions of the radiator. For example, the integral values along the strips $P_6$, $P_5$, $P_4$ are formed by interpolation of measuring values recorded in the positions A and B of the radiator. The integral values of the absorption along the strips $P_3$, $P_2$, $P_1$ are formed by interpolation of measuring values recorded in the positions B and C of the radiator. The integral value of the absorption along the straight line or strip $P_0$ is formed exclusively by a measuring value recorded in the position C. This is because the straight line $P_0$ passes exactly through the point C.

As has already been stated, for example, the measuring values recorded in the position B of the radiator are used for measuring the integral values of the absorption along the strips $P_6 \ldots P_1$. However, use is made only of the measuring values recorded in the position B which fall on a straight line, in the area determined by the parallel lines $P_6 \ldots P_1$, which passes through the center of rotation Z perpendicularly to the parallel strips. For measuring the parallel lines shown, therefore, always, only a part of the measuring values recorded in the positions A to E is used, i.e. the part which has been measured along straight lines or strips situated within the section of the radiation beam denoted by non-interrupted lines (the other measuring values are required for the interpolation of parallel extending sets which cross the parallel extending set shown at an angle).

The measuring values recorded in the other positions, for example, in the positions F and G, are not required for measuring the integral values along the set of parallel extending strips shown. These values are used when the integral values of parallel extending sets which intersect the body at a different angle are to be measured.

FIG. 2 shows how the integral value is formed from the measuring values. The references A to G in FIG. 2 again denote the various positions which can be occupied by the radiator on the arc. Moreover, the references $S_a$, $S_b$, $S_c$ denote the series of radiation detectors (which need not necessarily form a straight line, but which may also be an arc about the radiator) in the angular positions corresponding to the positions A, B and C. It is assumed that — contrary to FIG. 1 — the series of radiation detectors is arranged in the center of rotation Z of the radiator/radiation detector system; the description is thus simplified, because according to this representation the center of the series of detectors is not shifted when the radiator/radiation detector system is rotated; however the results obtained on the basis of FIG. 2 are of general validity. The reference $S_c$ at the same time denotes a straight line which passes through the axis of rotation Z and which extends perpendicularly with respect to the axis of rotation Z and the set of parallel extending lines $P_6 \ldots P_{-6}$.

The reference $P_5$ in the drawing denotes one of the parallel extending strips whose integral value is to be calculated. The strip or straightline $P_5$ extends between the two positions A and B. As a result, for the (linear) interpolation of the integral value along this straight line measuring values are used which have been recorded in the positions A and B of the radiator. In accordance with FIG. 2, these are the measuring values which have been recorded along the straight connection lines $M_a$ and $M_b$ between the positions A and B, respectively, and the intersection of the parallel line $P_5$ with the straight line $S_c$. As appears from the drawing, the straight lines $M_a$ and $M_b$ do not intersect the associated series $S_a$ and $S_b$, respectively, of detectors exactly at the area of the radiation detector 5, but rather further outwards. The integral value of the absorption along the straight lines $M_a$ and $M_b$, therefore, must also be measured by linear interpolation between the measuring values of the fifth and the sixth radiation detector. The integral value $IP_5$ of the absorption along the strip $P_5$ is thus obtained according to the formula: $IP_5 = M_{a5} \cdot G_1 + ?_{a6} \cdot G_2 + M_{b5} \cdot G_3 \cdot M_{b6} \cdot G_4$. Therein, $M_{a5}$ is the measuring value recorded by the fifth radiation detector in the position A of the radiator, and $M_{b6}$ is the measuring value recorded by the sixth radiation detector in the position B of the radiation source etc. The factors $G_1$, $G_2$, $G_3$, $G_4$ are weighting factors which relate to the geometrical relationships. The sum of $G_1$ and $G_2$ relates to the sum of $G_3$ and $G_4$ as the distance between the parallel line and B relates to the distance between the parallel line and A. Therefore, the nearer the parallel line passes along one of the two radiator positions, the larger the weighting factor of the measuring values taken into account for the calculation of the integral value. Moreover, for example, the factor $G_1$ is larger in comparison with the factor $G_2$ as the straight line along which the measuring value $M_{a5}$ has been recorded corresponds better to the straight line $M_a$; the same is applicable to the relationship between $G_3$ and $G_4$. Finally, the sum of all four factors always equals 1.

It appears from the equation that the integral value of the absorption in the body along one of the parallel lines can be calculated as the weighted sum of four measuring values. Accordingly, for example, the integral value along the parallel extending strip $P_4$ is calculated using the formula:

$$IP_4 = M_{a4} \cdot G_5 + M_{a5} \cdot G_6 + M_{b4} \cdot G_7 + M_{b5} \cdot G_8.$$

The weighting factors $G_5 \ldots G_8$ generally differ from the weighting factors $G_1 \ldots G_4$. Because the parallel line $P_4$ extends nearer to the position B of the radiator than the parallel extending strip $P_5$, the effect of the measuring values recorded in the position B of the radiator will be greater, with the result that the quotient $(G_5 + G_g) / (G_7 + G_8)$ will be smaller than the quotient $(G_1 + G_2) / (G_3 + G_4)$. It also appears from the two equations that each measuring value (in this case the measuring values $M_{a5}$, $M_{b5}$) is generally required for the calculation of two integral values (when the distance of two parallel extending strips corresponds to the distance of two radiation detectors). Similarly, the integral values along the other parallel extending strips can be calculated, the weighting factors then generally being mutually different. However, because the connection line between the radiator position C and the center Z is at the same time the symmetry line of the configuration, the weighting factors on the other side of the symmetry line are repeated in a mirrored manner; consequently, for example, the measuring value $M_{e-5}$ of the radiation detector $-5$ has the same weighting factor in the radiator position E for calculating the integral value along the parallel extending strip $P_{-5}$ as the measuring value $M_{a5}$ for the calculation of the integral value along the straight line $P_5$.

For the calculation of the integral values along a set of parallel extending strips which intersect the set of parallel lines of FIG. 1 at an angle which corresponds to the angle of rotation of the radiator between two neighbouring positions, for example, the positions C and D, the same weighting factors can be used; however, the measuring values recorded in one of the two extreme radiator positions, for example, the radiator position A, are then no longer required for the calculation. The measuring value recorded in the position F must then be used, instead.

Figure 3:
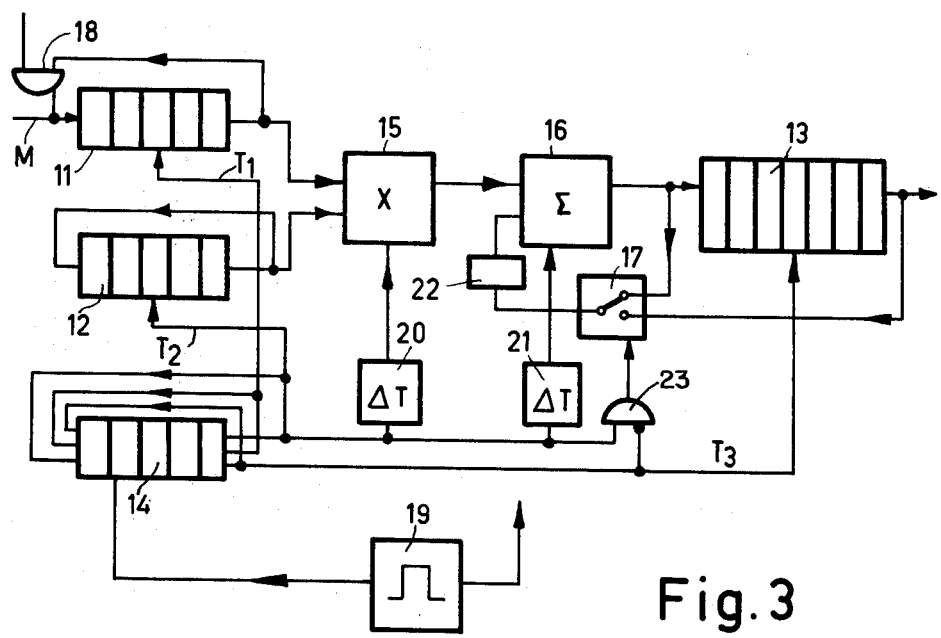
FIG. 3 shows a calculating circuit for calculating the integral values.

FIG. 3 shows a block diagram of a calculating circuit which is suitable for calculating the integral values on the basis of the measuring values. It is assumed that the measuring values recorded by the radiation detectors of the series of radiation detectors after the irradiation of the object layer are temporarily stored in a data register, while the radiator/radiation detector system has already been rotated further to the next recording position and has measured the next set of measuring values, so that the measuring values in the different radiator positions become successively available at regular instants. If the calculating circuit is capable of performing the calculation of the integral values of the absorption along a set of parallel extending strips and of applying the calculated values to the calculating device while the next set of measuring values is being recorded, and if the calculation of the set of parallel extending strips is effected at equidistant angular distances equal to the angles of rotation between the positions of the radiator, a fast and continuous flow of information from the measuring system to the calculating device is ensured and the intermediate storage of larger quantities of data will not be necessary.

The calculating circuit consists of three sequentially constructed information word stores 11, 12 and 13, three sequentially constructed, equally long binary registers, combined in the block 14, a multiplier circuit 15, a summing circuit 16, and a control circuit 19. The measuring values successively recorded in the radiator positions A ... E are stored in the store 11, so that the first measuring value ($M_{a6}$) in the first radiator position (A) is directly present on the output of the sequential store 11, while the last measuring value is present directly in front of the first measuring value ($M_{b6}$) recorded in the next radiator position, the subsequent values being stored in a corresponding order. The store 13 serves for the storage of the (approximated) integral values of the absorption along parallel extending strips, while the store 12 serves for storing the weighting factors required for the calculation.

The calculation is effected so that the contents of the stores 11, 12 and 13 are shifted in the direction of their output by means of clock pulses via the clock pulse lines $T_1$, $T_2$ and $T_3$. The values instantaneously present on the outputs of the stores 11 and 12 are returned to the corresponding store inputs and are simultaneously multiplied by each other by means of the multiplier circuit 15. The product is input into the store 13 via the summing circuit 16.

It is assumed that at a given instant during the calculating process the measuring value $M_{a5}$ is present on the output of the store 11. The weighting factor $G_1$ is then present on the output of the store 12. The product is added, in the summing circuit 16, to the product ($M_{a6} \cdot G_2$) present in an intermediate store 22 and is stored in the store 13 which comprises a storage position for each integral value of a number of parallel lines. After that, via the line T2 a shift pulse is applied to the sequential store 12, after which the weighting factor $G_2$ appears on the output thereof, while the measuring value $M_{a5}$ is present on the output of the store 11. This product is applied, via the summing circuit 16 and the switch 17, to the intermediate store 22. This intermediate storage by means of the switch 17 is always effected by gate 23 if a clock pulse appears on the line $T_2$ but not on the line $T_3$. Subsequently, clock pulses on the lines $T_1$, $T_2$ and $T_3$ shift the contents of the stores 11, 12 and 13 one position further in the direction of output. The measuring value $M_{a4}$ then appears on the output of the store 11, while the weighting factor $G_5$ appears on the output of the store 12. The product of these two values is added to the value present in the intermediate store 22 (resulting in the sum $M_{a4} \cdot G_5 + M_{a5} \cdot G_6$ for the calculation of the integral value along the parallel extending strip $P_4$) and is stored in the store 13. This is effected without interruption for all measuring values recorded in the radiator position A, in as far as they are required for the approximate calculation of the integral values (i.e. for the measuring values recorded within the radiation beam denoted by uninterrupted lines in FIG. 1). Subsequently, under the influence of an uninterrupted series of clock pulses on the line $T_1$, the contents of the store 11 are shifted so that all measuring values recorded in the radiator position A are present in the section of the store 11 on the input side, while the first measuring value ($M_{b6}$) recorded in the radiator position B is present on its output, a non-interrupted series of clock pulses on the line $T_3$ shifting the contents of the store 13 until the original storage position has been reached again. The measuring values recorded in the position B are treated in the same manner, the contents of the store 13 being applied, via the switch 17, to the second input of the summing circuit if clock pulses appear on both clock lines $T_2$ and $T_3$; inter alia the sum $M_{b4} \cdot G_7 + M_{b5} \cdot G_8$ is then added to the contents ($M_{a4} \cdot G_5 + M_{a5} \cdot G_6$) of this store associated with the integral value $IP_4$.

After all measuring values recorded in the radiator positions A ... E have been processed in the described manner, the contents of the store 11 and the contents of the store 12 will be in same storage positions again as at the start of the calculation, and the store 13 will contain the completed, calculated approximate integral values for transfer to the next section of the calculating circuit.

Before the approximate calculation of the integral values of the absorption along a further set of parallel extending strips can be effected, the measuring values recorded in the next position F of the radiator must be written in the store 11. This is effected by way of a non-interrupted series of clock pulses via the line $T_1$, with the result that the contents of the store 11 are shifted to the right and the new measuring values are taken up via the input line of the store. The gate 18 is then blocked, so that the measuring values recorded in the position A are shifted out of the store and are no longer available.

FIG. 4 shows the pulses on the clock lines $T_1$, $T_2$ and $T_3$ viewed in the time. It appears that until the instant $t_1$ the number of pulses on the clock line $T_2$ for the weighting factors is twice as large as the number of clock pulses on the clock lines $T_1$ and $T_3$ for the measuring value store and the integral value store, respectively. The pulses on the clock lines $T_1$ and $T_3$ have been shifted over one half period with respect to each other.

This clock pulse pattern can be explained in that — as has already been stated — one measuring value is used for calculating two integral values with different weighting factors; consequently, two weighting factors must be present for each measuring value, and between two measuring values, i.e. between two clock pulses on the line $T_1$, the integral value store must be shifted over one position (via $T_3$) in order to add the second product of the measuring value with a weighting factor (for example, $M_{a5} - G_1$) to the next integral value ($IP_5$). This pulse pattern is periodically repeated until the instant $t_1$.

At the instant $t_1$ a change occurs which is determined by the fact that the preceding measuring value is required only for the calculation of a single integral value; this can occur at given intervals due to the geometry of the measuring device. In order to prevent that this measuring value participates a second time in the calculation, an additional pulse is applied via the clock line $T_1$, with the result that the next measuring value is then ready for the calculation.

As has already been stated, not all measuring values are required for the calculation of the integral values along a set of parallel extending strips. Therefore, the weighting factor 0 would have to be assigned to these measuring values, because they are not involved in the further calculation. However, on the one hand this would require substantial storage space and on the other hand it would be time consuming. Therefore, for measuring values which are not required for the calculation, the section of the shift register 14 which supplies the clock pulses is programmed so that then no clock pulse appears on the clock line $T_2$. In that case there will not be a multiplication either by the measuring values continuously shifted by the pulses on the clock line $T_1$, because due to the absence of clock pulses on the clock line $T_2$, the multiplier circuit 15, controlled by $T_2$, and the summing circuit are inactive. Simultaneously with the cyclical shifting of the contents of the measuring value store 11, the contents of the integral value store 13 are shifted.

The clock pulses for the multiplier circuit 15 and the summing circuit 16 are applied via delay members 20 and 21, respectively, in order to ensure that a multiplication is effected only after the shifting of the contents of the stores 11 and 12 and that the sum is formed only after the multiplication has taken place.

It has thus far been assumed that neighbouring sets of parallel strips always intersect at the same angle about which the radiator/radiation detection system is rotated in the case of a change over from one measuring position (for example, position A) to an other measuring position (for example, position B). This has the advantage that the same set of weighting factors and clock pulse patterns can be used for each calculation and that during the calculation no exchange of the corresponding information sets need take place between the calculating unit and a higher-order testing computer, which would cause substantial delays. Without prejudice to the foregoing, however, it is also possible to calculate the integral values of the absorption along further sets of parallel extending strips whose angular positions are situated, for example, exactly between those of the radiators. It is thus also posible, for example, to double the number of sets of strips along which the absorption is to be calculated, with the result that the accuracy of the absorption calculation for the relevant body section is improved. A second set of weighting factors and clock pulse patterns is then required; this set must be alternated with the first set. This can be taken into account in the circuit shown in FIG. 3 in that the length of the registers 12 and 14 is about doubled, so that both sets of information can be consecutively stored. The completion of the calculation is then changed so that after the calculation of a set of parallel extending strips at a given angular position corresponding to that of a radiator, the information values have occupied the same positions again in the stores 11 and 13 as before the calculation, but that the values in the stores 11 and 14 have been shifted only over half the register length.

For the sake of simplicity it has thus far been assumed that the distance between two strips corresponds to the distance between two detectors. However, this is not necessarily so, because the difference in number can be compensated for by modified weighting factors and clock pulse patterns. It may notably be useful to vary the diameter of the detectors through the series of detectors, in order to allow better adaptation of the measuring system to the geometry of given kinds of body.

It has thus far been assumed that the radiator/radiation detector system is rotated exactly through a predetermined angle between two different positions, for example, the positions B and C. However, this condition cannot be completely satisfied in all cases. Therefore, it may be advantageous to provide an additional calculating unit which calculates the weighting factors each time in dependence of the actual rotation of the radiator/radiation detector system.

What is claimed is:

1. A device for measuring radiation absorption in a section of a body, comprising a radiation source emitting a wedge-shaped flat beam which irradiates the body, a series of adjacently arranged radiation detectors for the local measurement of a transmitted part of the radiation in different positions of the source and the detectors with respect to the body, means for calculating the absorption in the section to be measured on the basis of the measuring values obtained, and means to calculate integral values of the absorption along mutually crossing sets of mutually parallel extending strips by interpolation of measuring values, the integral values being processed by the means for calculating the absorption in the section of the body.

2. A device as claimed in claim 1, wherein the radiator/radiation detector system is rotatable through an angle of not more than 180° for measuring the measuring values, and the means to calculate the absorption forms the integral values by interpolation of measuring values recorded in two adjoining positions between which the strip each time extends.

3. A device as claimed in claim 1, in which the radiator/radiation detector system is rotatable through an angle of more than 180° for measuring the measuring values, wherein the means for calculating the absorption forms the integral values by interpolation of measuring values recorded in four positions each time two positions thereof being adjacent and enclosing the strip to be calculated.

4. A device as claimed in claim 3, wherein the interpolation is effected on the basis of the measuring values recorded along straight lines which intersect the strip to be calculated in a straight line which is perpendicular to the strip and which extends through the point of rotation of the system.

5. A device as claimed in claim 4 wherein the measuring value is formed by interpolation between two measuring values recorded along straight lines which intersect the straight line on both sides of the strip.

6. A device as claimed in claim 5 wherein the means to calculate integral values of the absorption comprises two sequentially constructed information word stores one of which stores the measuring values obtained in different positions of the radiation source, while the other store stores the weighting factors which are dependent on the geometrical relationships, and includes multiplier means which multiplies the values each time present on the output of the information word stores by each other, and summing means which sums the products obtained to form further products each time assigned to the integral value and which stores these values in store means which comprises a storage position for each integral value to be calculated.

7. A device as claimed in claim 6, wherein one of said information word stores for the weighting factors stores only the weighting factors other than 0, and includes clock means producing pulses which serve for shifting the contents of said information word stores and for timing the multiplier means, and means timing the summing means and the multiplier means with respect to each other so that, in the case of a weighting factor 0, the information word store for the measuring values receives a clock pulse, while the information word store for the weighting factors and the information word store means for the integral values do not receive a clock pulse, the multiplier means and the summing means then being blocked..

8. A device as claimed in claim 6, in which one measuring value is used for calculating at the most two integral values of the absorption along a set of parallel extending strips, wherein the number of clock pulses for the information word store for the weighting factors is twice as large as the number of clock pulses for the information word stores for the measuring values and the integral values, respectively, the information word store for the measuring values receiving an additional clock pulse if a measuring value is required only for calculating a single integral value.

9. A device as claimed in claim 6, including a clock pulse generator, three shift registers for generating clock pulses from said clock pulse generator, one of said shift registers supplying clock pulses for the information word store for the measuring values, a second of said shift registers supplying clock pulses for the information word store for the weighting factors and for the multiplier means and the summing means, and a third of said shift registers supplying clock pulses for the store for the integral values.

10. A device as claimed in claim 9, wherein the contents of the three shift registers and the contents of the information word store for the weighting factors can be externally modified.

11. A device as claimed in claim 6, in which the measuring values are recorded from equidistant angular positions and in which the sets of parallel extending strips are calculated for equidistant angular positions, the angular difference between each time two positions being twice as large as the angle at which two adjacently positioned sets of parallel extending strips intersect each other.

* * * * *